United States Patent
Venkatesh et al.

US006184430B1

(10) Patent No.: US 6,184,430 B1
(45) Date of Patent: *Feb. 6, 2001

(54) HYDROCRACKING AND HYDROISOMERIZATION OF LONG-CHAIN ALKANES AND POLYOLEFINS OVER METAL-PROMOTED ANION-MODIFIED TRANSITION METAL OXIDES

(75) Inventors: Koppampatti R. Venkatesh, Pittsburgh, PA (US); Jianli Hu, Cranbury, NJ (US); John W. Tierney; Irving Wender, both of Pittsburgh, PA (US)

(73) Assignee: The United States of America as represented by the United States Department of Energy, Washington, DC (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/761,764

(22) Filed: Dec. 5, 1996

(51) Int. Cl.$^7$ ................................ C07C 5/22; C07C 4/06
(52) U.S. Cl. .................... 585/750; 585/752; 585/671; 208/108; 208/112
(58) Field of Search .................... 208/108, 112, 208/46; 585/750, 751, 752, 671

(56) References Cited

U.S. PATENT DOCUMENTS

| | | | |
|---|---|---|---|
| 4,918,041 | * 4/1990 | Hollstein et al. | 502/217 |
| 5,036,035 | * 7/1991 | Baba et al. | 502/221 |
| 5,120,898 | * 6/1992 | Baba et al. | 585/750 |
| 5,157,199 | * 10/1992 | Soled et al. | 585/750 |
| 5,304,696 | * 4/1994 | Khare et al. | 585/668 |
| 5,391,532 | * 2/1995 | Soled et al. | 502/210 |
| 5,422,327 | * 6/1995 | Soled et al. | 502/242 |
| 5,489,733 | * 2/1996 | Soled et al. | 585/740 |
| 5,494,569 | * 2/1996 | Umansky et al. | 208/108 |
| 5,510,309 | * 4/1996 | Chang et al. | 208/46 |
| 5,516,964 | * 5/1996 | Umansky et al. | 585/751 |
| 5,629,257 | * 5/1997 | Umansky et al. | 502/217 |
| 5,648,589 | * 7/1997 | Soled et al. | 585/734 |
| 5,719,097 | * 2/1998 | Chang et al. | 502/325 |
| 5,780,382 | * 7/1998 | Chang et al. | 502/309 |
| 5,780,703 | * 7/1998 | Chang et al. | 585/732 |
| 5,854,170 | * 12/1998 | Chang et al. | 502/308 |
| 5,902,767 | * 5/1999 | Kresge et al. | 502/308 |
| 5,993,643 | * 11/1999 | Chang et al. | 208/59 |

OTHER PUBLICATIONS

"Sulfated Metal Oxides and Related Solid Acids: Comparison of Protonic Acid Strength," Koppampatti R. Venkatesh, Jianli Hu, Celal Dogan, John W. Tierney and Irving Wender, Energy & Fuels, 888–893, 9 (1995). (No Month).

"Reactions of aromatics and naphthenes with alkanes over at Pt/ZrO$_2$SO$_4$ catalyst," J. Hu, K.R. Venkatesh, J.W. Tierney and I. Wender, Applied Catalysis A: General, L179–L186, 114 (1994). (No Month).

"Hydroisomerization and Hydrocracking of n–Heptane and n–Hexadecane on Solid Superacids," Michael Y. Wen. Irving Wender and John W. Tierney, Energy & Fuels, 372–379, 4 (1990). (No Month).

* cited by examiner

Primary Examiner—Walter D. Griffin
(74) Attorney, Agent, or Firm—Mark LaMarre; Mark P. Dvorscak; William R. Moser

(57) ABSTRACT

A method of cracking a feedstock by contacting the feedstock with a metal-promoted anion-modified metal oxide catalyst in the presence of hydrogen gas. The metal oxide of the catalyst is one or more of ZrO$_2$, HfO$_2$, TiO$_2$ and SnO$_2$, and the feedstock is principally chains of at least 20 carbon atoms. The metal-promoted anion-modified metal oxide catalyst contains one or more of Pt, Ni, Pd, Rh, Ir, Ru, (Mn & Fe) or mixtures of them present between about 0.2% to about 15% by weight of the catalyst. The metal-promoted anion-modified metal oxide catalyst contains one or more of SO$_4$, WO$_3$, or mixtures of them present between about 0.5% to about 20% by weight of the catalyst.

27 Claims, 11 Drawing Sheets

HYDROCRACKING AND HYDROISOMERIZATION OF LONG-CHAIN ALKANES AND POLYOLEFINS OVER METAL-PROMOTED ANION-MODIFIED TRANSITION METAL OXIDES

CONTRACTUAL ORIGIN OF THE INVENTION

The United States Government has rights in this invention pursuant to Contract No. W-31-109-ENG-38 between the U.S. Department of Energy and The University of Chicago representing Argonne National Laboratory.

BACKGROUND OF THE INVENTION

The desire to produce highly isomerized alkanes for high-octane transportation fuels has led to the use of bifunctional catalysts containing dispersed transition metals on acidic supports for alkane hydrocracking, as reported by Sullivan, F. R., Meyer, J. A. ACS Symp. Ser. 1975, No. 20, 28. Bifunctional catalysts consisting of hydrogenation components such as sulfided Ni, Mo, or W promoted on acidic supports such as $Al_2O_3$ or $SiO_2$—$Al_2O_3$ have been used; they crack n-alkanes to a significant extent but result in little isomerization. Noble metals, such as Pt and Pd, are strong hydrogenation catalysts which balance the acidity of supports and were reported to result in high selectivities to isomerized products in alkane hydrocracking, all as reported by W. A. van Hook and P. H. Emmett, *J. Am. Chem. Soc.* 1962, 14, 4410 and H. L. Conradt and W. E. Garwood, *Ind. Eng. Chem.* 1960, 52, 113. It was previously indicated that the amounts of isomerized and normal alkanes formed in n-alkanes hydrocracking depend on the relative strengths of the metal and acidic functions. Over the past two decades, a variety of Pt-promoted zeolites have been used as n-alkanes hydrocracking catalysts and have shown good selectivity to isokanes and increased resistance to heteroatom impurities.

Strong solid acid catalysts have high activity in cracking and skeletal isomerization of n-alkanes, as reported by Y. Nukano et al., *J. Catal.* 1979, 57, 1, J. C. Yori et al., *Catal. Today* 1989, 5, 493 and T. Hosoi et al., *Am. Chem. Soc. Div. Petr. Chem.* 1988, 562, and could serve as effective hydrocracking catalysts, especially when promoted by strong hydrogenation metals such as Pt and Ni. The metal-promoted anion-modified zirconium oxides (AZOs) such as $Pt/ZrO_2/SO_4$ and $Pt/ZrO_2/WO_3$, are strong solid acids with an active hydrogenation function; they could potentially replace the conventional bifunctional catalysts. There is increased interest in these catalysts because they have high activity at relatively low temperatures(<200° C.) favoring isomerization, are environmentally acceptable, are noncorrosive, are easily separated from process streams, and may be regenerated by calcination in air.

There has been much work reported on the use of these catalysts, especially sulfated zirconium oxide (SZO), for the isomerization of n-butane to isobutane, see T. Hosoi et al. *Am. Chem. Soc. Div. Petr. Chem.* 1988, 562, K. Tanabe et al., *Crit. Rev. Surf. Chem.* 1990, 1(1), 1, C. Morterra et al. Catal. 1994, 149, 181, F. Garin et al., *J. Catal,* 1991, 131, 199, P. Moles, Specialty Chemicals, Nov./Dec. 1992, M. A. Coehlo et al. *Catal. Lett.* 1995, 32, 253 and M. Hino et al., *Catal. Lett.* 1995, 30, 25, a reaction not catalyzed by 100% $H_2SO_4$. Since superacids have been defined as acids stronger than 100% $H_2SO_4$, the AZOs were considered to be solid superacids, but this classification is presently unsettled. Whether the activity and nature of acidity of these catalysts are attributable to Lewis or Bronsted acid sites or most likely to both is also under debate. Nevertheless, there is little doubt that carbocations are involved in most reactions catalyzed by AZOs. Pt-promoted SZO is reportedly a more active catalyst for higher alkane cracking and isomerization than most zeolite-based catalysts, see B. H. Davis et al., *Catal. Today* 1994, 20, 219.

Since there is a move to decrease aromatics and olefins in gasoline, the virtual absence of these compounds in the products may be an advantage of AZOs over zeolites. The cracked products obtained using SZOs also have more highly branched isoalkanes than those obtained using zeolites, since lower temperatures favor isomerization. M. Y. Wen et al. *Energy & Fuels* 1990, 4, 372, showed that $Pt/ZrO_2/SO_4$ and Pt-promoted sulfated mixed oxides of zirconium and hafnium were active for the hydrocracking and hydroisomerization of n-heptane and n-hexadecane at 160° C. and 360 psig (cold) $H_2$. The Pt-SZO catalysts were also found to be active for reactions such as hydrocracking of the alkyl chain in long-chain alkylaromatics and for the alkylation of aromatics with alkanes.

SUMMARY OF THE INVENTION

We have found that polymers of widely varying chain lengths, from n-$C_{20}$ to Fischer-Tropsch (F-T) waxes ($C_{58}$–$C_{64}$), and even long-chain polyolefins such as polyethylene and polypropylene, could be hydrocracked in a single step to produce either gasoline-range isoalkanes or a mixture of isobutane and isopentane over AZOs. Hydrocracking of long-chain polyolefins to transportation fuels could serve to reduce the large amounts of plastic wastes now consigned to landfills in the United States. While metal-promoted AZOs are dual-functional, results indicate that hydrocracking of long-chain n-alkanes ($C_{20}$ and higher) over these catalysts may not involve the conventional bifunctional mechanism in which the metal plays a dehydrogenation-hydrogenation role resulting in olefinic precursors to carbocations.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

DETAILED DESCRIPTION OF THE INVENTION

Figure 1:
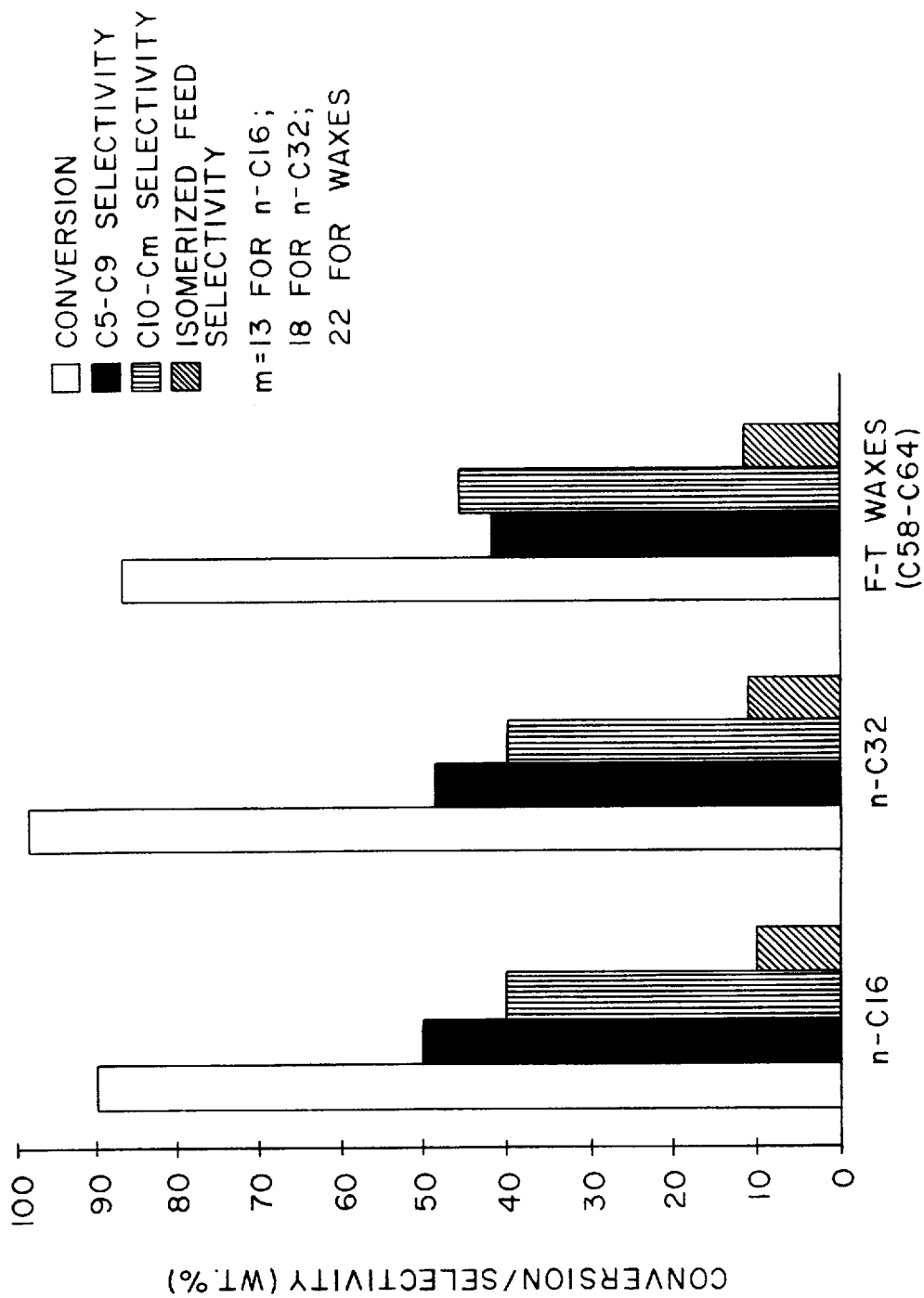
FIG. 1 is a graphical representation of the hydrocracking and hydroisomerization of long-chain alkanes over SZPt0.5 using 360 psig (cold) $H_2$, 60 min. (cat./n-$C_{16}$=⅙, cat./n-C32=⅓, cat/F-T waxes=⅓, 160° C. for n-C16, 170° C. for n-C32 and F-T waxes)

The SZOs were prepared by the hydrolysis of zirconium sulfate [$H_2ZrO(SO_4)_2 3H_2O$, Pfaltz & Bauer, 99%] with aqueous ammonia (28% $NH_4OH$, Fisher Scientific) at room temperature followed by filtration. The resulting zirconium hydroxide [$Zr(OH)_4$] precipitate obtained was filtered and washed with double-distilled water to remove excess ammonium ions and then dried at 110° C. Sulfation of the hydroxide was carried out by adding 1.0 N sulfuric acid (10 mL of acid/g of precipitate) with constant stirring. After the sulfated material was dried overnight at 110° C., it was ground to smaller than 100 mesh and calculated amounts of Pt or Ni were impregnated using either chloroplatinic acid ($H_2PtCl_6 6H_2O$, Strem Chemical Co., 99.9% or nickel nitrate [$Ni(NO_3)_2 6H_2O$], Aldrich Chemical Co., 99.999%). They were then calcined at 630° C. in air for 3 hours. Tungstate-modified zirconia (WZO) was prepared using zirconium nitrate [$ZrO(NO_3)_2 H_2O$, Strem] as the starting salt to yield $Zr(OH)_4$. After repeated washing of the precipitate with warm (~50° C.) double-distilled water to remove $NO_3^-$-ions, calculated amounts of ammonium metatungstate [$(NH_4)_6W_{12}O_{40}$, Strem, 99.9+%] were used to impregnate the $Zr(OH)_4$ via the incipient wetness technique. The molar content of tungsten in $Pt/ZrO_2/WO_3$ was calculated to be the same as that of sulfur on $Pt/ZrO_2/SO_4$. The same procedure was used for incorporating $MoO_3$ on $ZrO_2$, using ammonium molybdate tetrahydrate (($NH_4)_6H_2Mo_7O_{24}$ $4H_2O$, Strem, 99.999%). Hydrogenation metals were incorporated using the same procedure as with SZO's and calcinations were carried out at 700° C. (for $WO_3$) and 800° C. (for $MoO_3$) in air for three hours.

The AZO's that were synthesized are identified by the coding system shown in Table 1.

TABLE 1

AZOs Synthesized In This Study and Their Abbreviated Codes

| catalyst | Pt or Ni content (wt %) | code |
|---|---|---|
| $Pt/ZrO_2/SO_4$ | 0.5 | SZPt0.5 |
| $Ni/ZrO_2/SO_4$ | 0.5 | SZNi0.5 |
| $Ni/ZrO_2/SO_4$ | 2.0 | SZNi2.0 |
| $Pt/ZrO_2/WO_3$ | 0.5 | WZPt0.5 |
| $Ni/ZrO_2/WO_3$ | 2.0 | WZNi2.0 |

The first letter of the code denotes the anionic group (S for $SO_4$ or W for $WO_3$), the second letter Z for the oxide support ($ZrO_2$) and the rest for the promoter metal (Pt or Ni) and its concentration in weight percent. BET surface areas of catalyst were measured using a Micromeritics ORR surface area and pore volume analyzer and XRD profiles were obtained with a Phillips XPert diffractometer using nickel-filtered Cu Kα radiation at 40 kV and 30 mA. X-ray absorption near edge spectroscopy (XANES) of catalyst was conducted at Brookhaven National Laboratory's NSLS X-19A using a Si(111) monochromator.

n-Heptane (n-$C_7$, 99%), n-hexadecane (n-$C_{16}$, 99%), n-dotriacontane (n-$C_{32}$, 97%), polypropylene (PP, isotactic, $M_{avg}$, ~280,000) were obtained from Aldrich. An F-T wax ($C_{58}$–$C_{64}$) was provided by SASOL. High density polyethylene (HDPE, $M_{avg}$~250,000, d=0.96 g/cc) was obtained from Solvay Polymers. The catalysts were activated at 450° C. in air just before reaction and charged immediately into an oven-dried (110° C.) 27 $cm^3$ stainless steel microreactor tubing bomb) and quickly sealed. After cooling to room temperature, the reactants were charged through the 15 $cm^3$ stem attached to the reactor unless otherwise specified. The reactor was heated to the desired reaction temperature in a fluidized sand bath while mixing of the reactor contents was provided by horizontal shaking at 200 cpm. Sulfur and tungsten analyses of the catalysts were performed by Galbraith Laboratories, Inc.

The products were analyzed using an HP 5890 Series II GC (FID) and HP 5970 GC-MS. Conversions were based on the amount of remaining alkane feed (for n-$C_7$, n-$C_{16}$ and n-$C_{32}$) or on the recovered solid material (for F-T waxes and polyolefins). Conversions and product selectivities could be reproduced within 2% and 3%, respectively. Thermodynamic isomerization equilibria of $C_4$–$C_7$ alkanes at reaction conditions were calculated using ASPEN Plus process simulation software at the University of Pittsburgh. Simulated distillations of the liquid products obtained from polyolefin hydrocracking were conducted using an HP 5890 Series II GC (TCD) controlled by an HP 3396A integrator programmed to run the ASTM D2887 distillation method in which the entire product mixture is dissolved in $CS_2$ to form a homogeneous mixture. The result is given as a series of boiling points, one after every 5 wt % of the sample is eluted.

TABLE 2

Physical Properties of AZOs

| Catalyst | S or W Content (wt %) | calcd temp (° C.) | BET surface area($m^2$/g) | av particle size(Å) | crystalline phase |
|---|---|---|---|---|---|
| SZPt0.5 | 1.63 | 630 | 102.5 | 90 ≠ 5 | tetragonal |
| WZPt0.5 | 7.07 | 700 | 62.0 | 92 ≠ 5 | tetragonal |
| $ZrO_2$ | 0 | 47 | 47 | 132 ≠ 5 | tetragonal |

The physical properties of some of the catalysts that were tested are shown in Table 2. Unmodified $ZrO_2$ was calcined at a different temperature than $SO_4$ or $WO_3$ modified catalysts. All of the catalysts then had the same tetragonal structure. $ZrO_2$ modified by $SO_4$ and $WO_3$ groups had BET surface areas significantly higher than those of unmodified $ZrO_2$ (Table 2). Modification of $ZrO_2$ by $WO_3$ resulted in a lower catalyst surface area compared to modification by $SO_4$. These observations are consistent with literature results.

Figure 2:
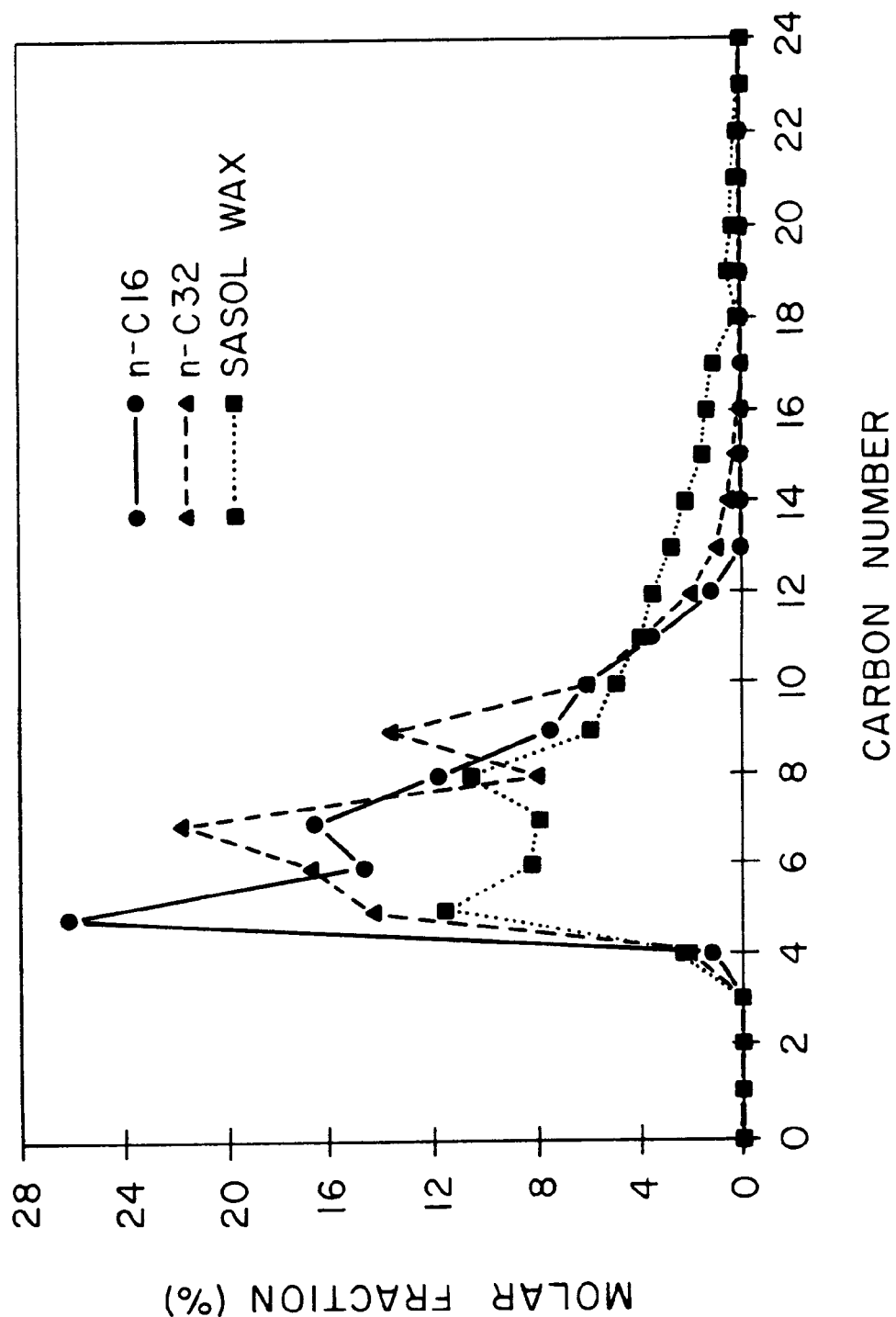
FIG. 2 is a graphical representation of the distribution of cracked products from hydrocracking of long-chain alkanes over the SZPt 0.5 catalyst (same reaction conditions as in FIG. 1)

Earlier work by Wen et al. and Keogh et al., see R. A. Keogh et al., *Energy & Fuels* 1994, 8, 755, showed that hydrocracking of n-$C_{16}$ over a SZPt0.5 catalyst at 160° C. and 350 psig (cold) $H_2$ resulted in high conversions and high yields of $C_4$–$C_9$ alkanes. We have found that these catalysts used with n-$C_{32}$ and F-T waxes ($C_{58}$–$C_{64}$), yield similar conversions and selectivities at 170° C. over a SZPt0.5 catalyst (FIGS. 1 and 2). Varying feed/catalyst ratios and temperature produces cracked alkanes in the $C_4$–$C_9$ range, regardless of the chain length of the feed alkane. As shown later, by increasing the reaction temperature and reaction time, the products from long-chain alkane hydrocracking consist primarily of gases with high selectivities to isobutane and isopentane. It has been reported that the rate of n-butane isomerization over Pt-SZO is enhanced by using a feed containing 33 ppm of butene as an impurity; the reaction order with respect to hydrogen was reported to be negative (−1.1 to −1.3). These results are consistent with the conventional bifunctional mechanism of butane isomerization over Pt-SZO. On the other hand, our results and those of Keogh et al. show that increasing $H_2$ pressures [from 14.7 to 1600 psig (cold)] increases n-$C_{16}$ conversion, indicating a positive reaction order relative to $H_2$. By adding an olefin of the same carbon number as the alkane feed, we found that the alkane hydrocracking activity of a SZPt0.5 catalyst is severely reduced (Table 3).

TABLE 3

Effect of Olefin Addition on n-C7 and n-C16 Hydrocracking over SZPt0.5 Catalyst

| feed | olefin | alkane conversion ($^a$wt %) |
|---|---|---|
| n-C7 | none | 75.0 |
| n-C7 | 1-heptene (0.6 wt %) | 3.0 |
| n-C7 | 1-heptene (50.0 wt %) | 0.0 |
| n-C15 | none | 75.4 |
| n-C16 | 1-hexadecene (1.5 wt %) | 59.9 |

Reaction conditions: (i) n-C7, feed/cat = 10/1, 150° C., 350 psig (cold) $H_2$, 60 min; (ii) n-C16, feed/cat. = 6/1, 160° C., 360 psig (cold) $H_2$, 60 min.

The added olefins were completely hydrogenated. This suggests that the olefins selectively adsorb onto acid sites which are then not available for further reaction. This inhibiting effect is less for n-$C_{16}$ than for n-$C_7$ because the difference in cracking activity of an alkane and its corresponding olefin decreases with increase in carbon number. Since the added alkenes inhibit the activity of the catalyst, hydrocracking of higher alkanes over Pt-SZO provides further evidence that carbenium ions may not be generated by olefinic precursors. Alkanes with carbon numbers exceeding the n-$C_7$ or n$C_{16}$ feeds were absent, a result that favors a unimolecular mechanism for hydrocracking of n-$C_{7+}$ alkanes over Pt-SZO catalysts. These observations suggest that the mechanism by which n-butane isomerization and hydrocracking occur differs from the mechanism by which the same reactions take place with higher alkanes. Pt-SZO does not seem to act as a conventional bifunctional catalyst for higher ($C_{7+}$) alkanes.

Although n-$C_7$ and n-$C_{16}$ alkanes react with certain zeolites to form aromatic or cyclic products, surprisingly no such compounds were found in our reaction products. Small amounts (1.4 wt %) of $C_7$, $C_8$ and $C_9$ cycloalkanes only from the reaction of polypropylene over SZPt0.5, were detected. These could possibly be formed by twisting of the long polymer chain, allowing interaction with reactive alkyl intermediates during hydrocracking of the polymers.

Figure 3:
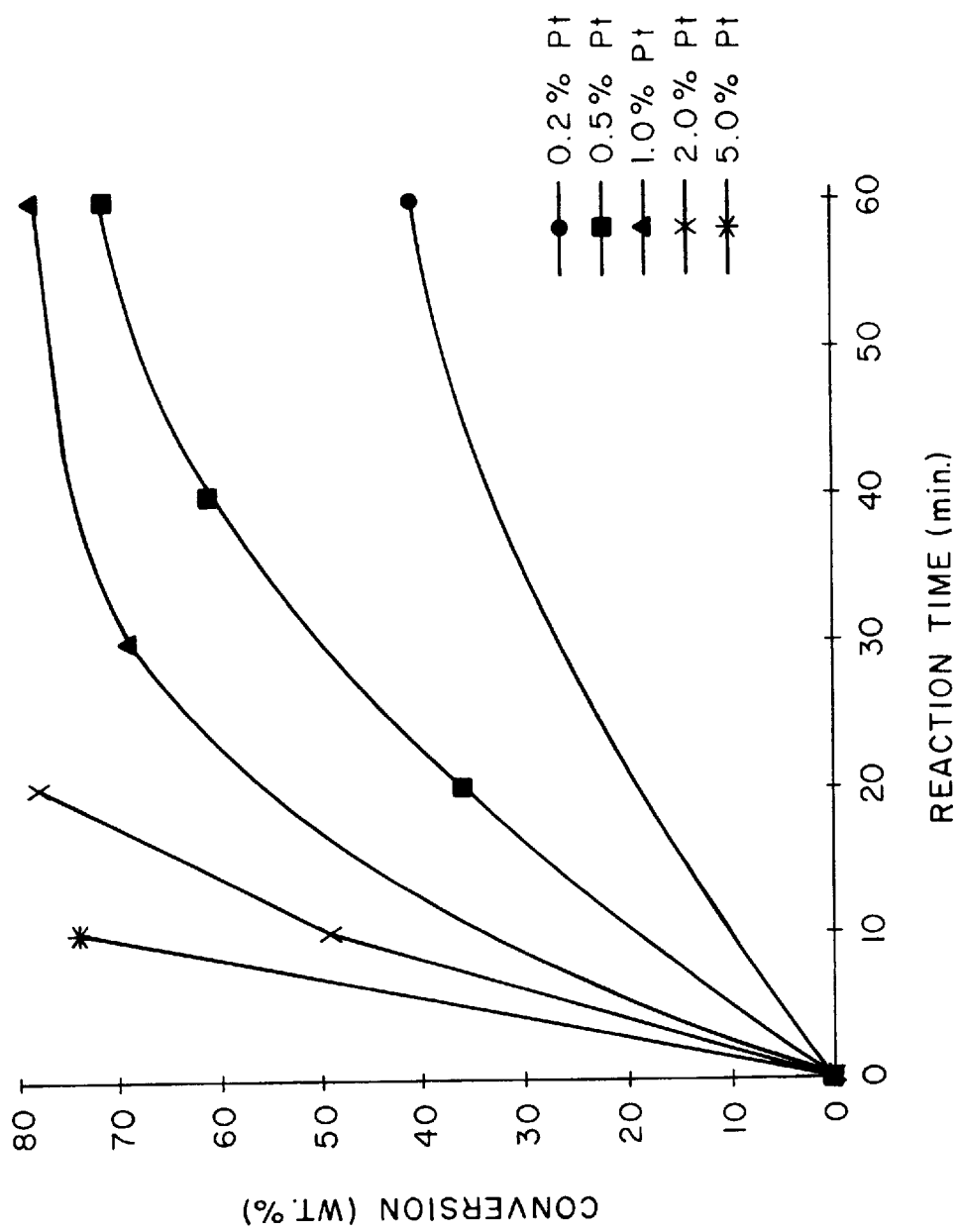
FIG. 3 is a graphical representation of the effect of increasing Pt content on the n-C16 hydrocracking activity of a SZPt0.5 catalyst where conditions were 160° C., 360 psig (cold) $H_2$, 60 min. cat./n-C16=⅙ by wt.
Figure 4:
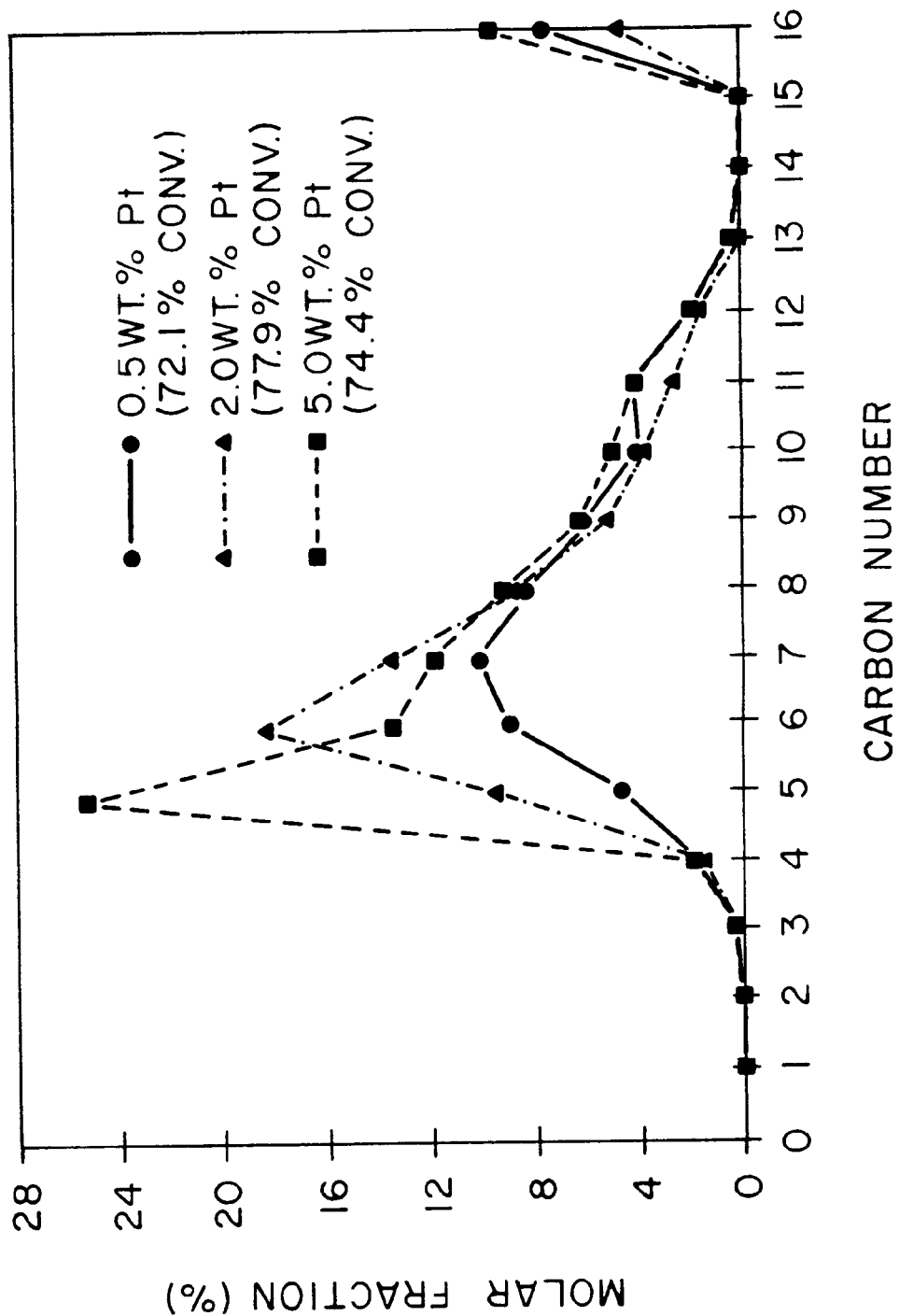
FIG. 4 is a graphical representation of the effect of Pt loading on the product distribution from n-$C_{16}$ hydrocracking over a SZPt0.5 catalyst (same reaction conditions as in FIG. 3)

Increasing the Pt content of sulfated zirconia results in higher conversions and higher yields of $C_4$–$C_9$, cracked products (FIG. 3). However, for reaction times of 60 minutes, the effect seems to be small at Pt concentrations exceeding 0.5 wt %, indicating that high hydrogenation activity and elimination of coke precursors are effectively achieved at this concentration and higher. The product distribution is shifted toward lower carbon numbers with a higher Pt content on the catalyst (FIG. 4), indicating that cracking activity is increased with increasing Pt content.

The effect of temperature on alkane hydrocracking activity of SZPtP0.5 is shown in Table 4.

TABLE 4 n-Hexadecane Hydrocracking over an SZPt0.5 Catalyst

| | 160° C. | 300° C. | 350° C. |
|---|---|---|---|
| conversion (wt %) | 75.4 | 76.2 | 77.3 |
| product range | selectivity (wt %) | | |
| $C_4$–$C_9$ | 67.8 | 81.1 | 88.2 |
| $C_{10}$–$C_{13}$ | 23.4 | 10.8 | 9.4 |
| iso–$C_{16}$ | 9.8 | 8.1 | 2.4 |

360 psig (cold) $H_2$, 60 min. 500 psig (cold) $H_2$, 20 min. 500 psig (cold) $H_2$, 20 min. No. C1, C2, C14 or C15 was formed in reactions at 160° C., but small amounts were detected at 300 and 350° C.

Figure 5:
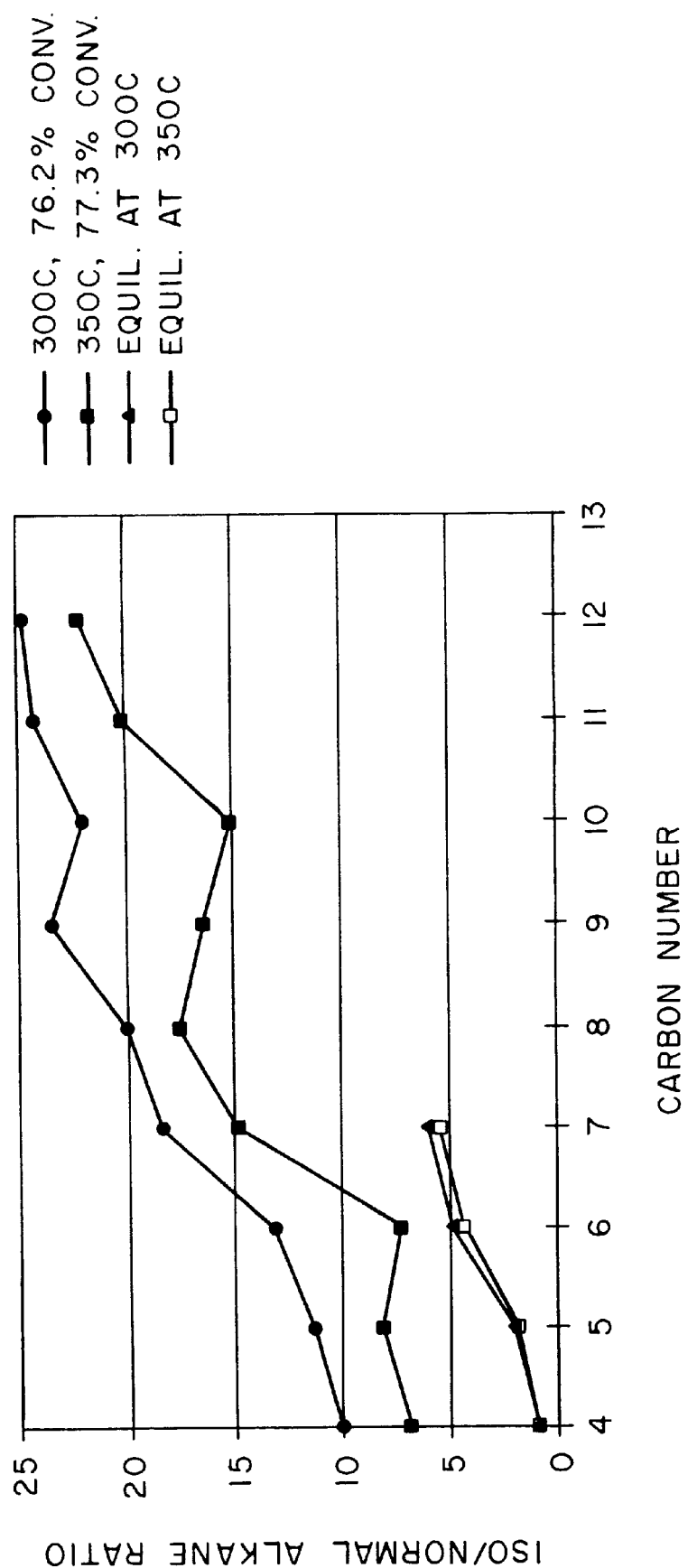
FIG. 5 is a graphical representation of the iso/normal alkane ratio of cracked products from n-$C_{16}$ hydrocracking over SZPt0.5 under 500 psig (cold) $H_2$ and 20 min. reaction time.

The reaction conditions were adjusted to achieve similar levels of conversion at three different temperatures to compare product selectivities at the same extent of reaction. At higher temperatures, the product distribution from hydrocracking of n-$C_{15}$ over SZPt0.5 shifts towards cracked $C_4$–$C_9$, alkanes with a corresponding loss in the yield of iso-$C_{16}$. The relative yield of the more desirable isomerized alkanes with respect to normal alkanes for each carbon number of the products is shown in FIG. 5. The iso/normal alkane ratios of the cracked products obtained at these high temperatures are higher than those predicted by thermodynamic isomerization equilibria. This may be due to greater kinetic stability of the branched (tertiary or secondary) carbocations compared to primary cations, resulting in faster desorption of these branched cations by hydride transfer. The iso/normal ratio increases significantly as a function of carbon number, indicating that isomerization of higher alkanes precedes cracking.

By increasing the reaction temperature and reaction time as shown in Table 5 (compare with conditions in FIGS. 2 and 3), the product distribution from long chain alkanes is shifted to $C_1$–$C_5$. alkanes, of which more than 78 mol % consisted of iso-$C_4$ and iso-$C_5$. This is due to the further cracking of the heavier products ($C_6$+ isoalkanes) formed in reactions at mild conditions. Small amounts of methane and ethane were formed in these reactions.

TABLE 5

Synthesis of Isobutane and Isopentane from n-$C_{16}$ and an F-T Wax over a SZPt0.5 Catalyst

|  | n-$C_{16}$ | F-T wax |
|---|---|---|
| product range | yield (wt %) | |
| C6–Cx alkanes | 18.5 | 3.5 |
| C1–C5 alkanes | 80.2 | 95.5 |
| product | selectivity (mol %) | |
| methane + ethane | 0.5 | 1.5 |
| propane | 2.5 | 6.9 |
| isobutane | 43.0 | 48.0 |
| n-butane | 1.8 | 3.9 |
| isopentane | 42.3 | 30.7 |
| n-pentane | 9.9 | 9.0 |

[a]Reaction conditions: (i) n-C16, 375° C., 750 psig (cold), $H_2$, 60 min. feed/cat. = 6/1; (ii) F-T wax, 375° C., 1200 psig (cold) $H_2$, 60 min. feed/cat. = 5/1, [b] x = 15 for n-$C_{16}$; x = 20 for F-T wax.

Figure 6:
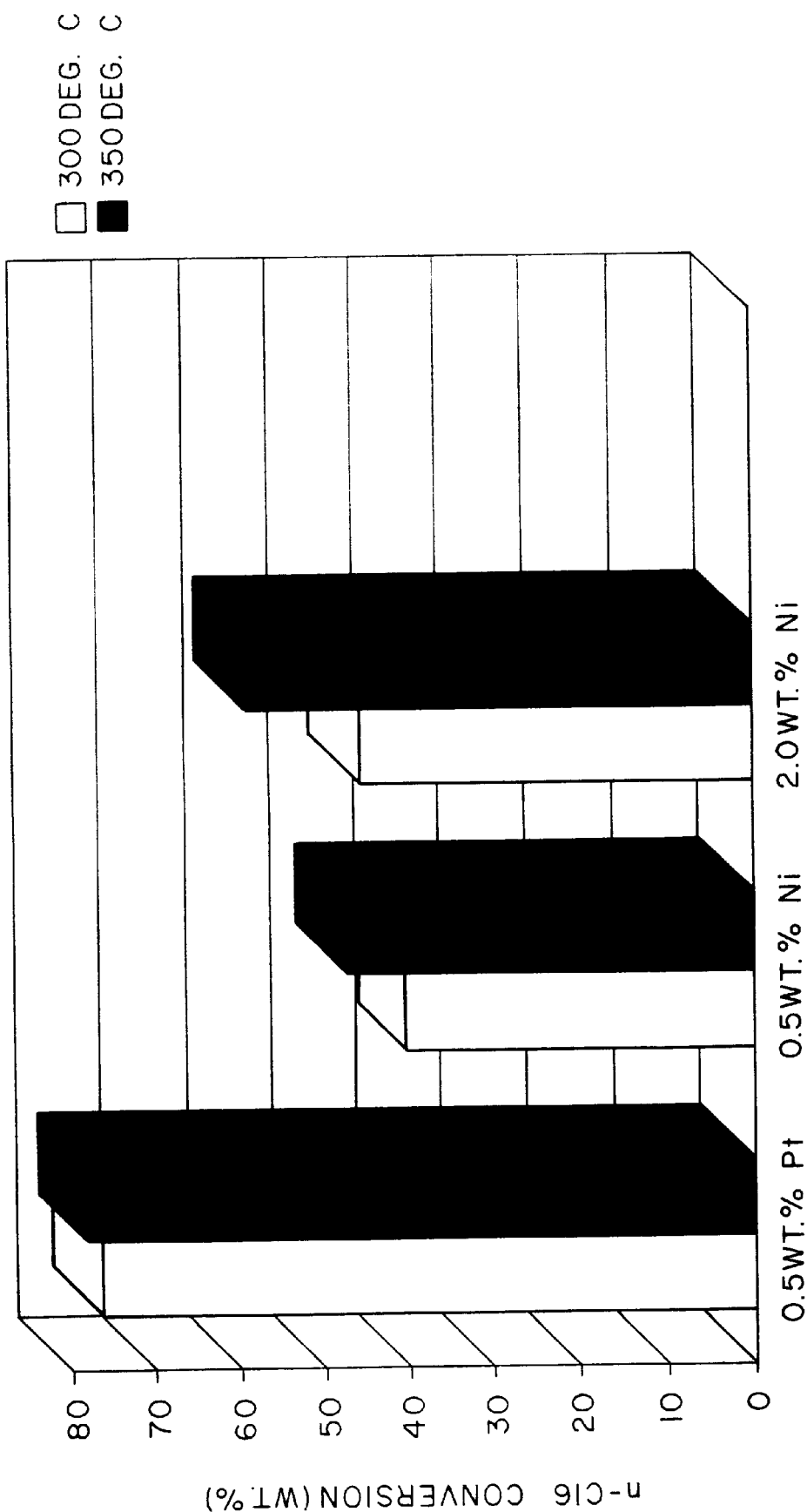
FIG. 6 is a graphical representation of the effect of Ni promotion on n-$C_{16}$ hydrocracking activity of SZO as compared with SZPt0.5. $H_2$ pressures and reaction times were 500 psig (cold) and 20 min., respectively.

Effects of various promoter metal and anionic components of AZOs on the hydrocracking activity of n-$C_{16}$ were investigated. Conversions obtained using nickel as compared to platinum for n-$C_{16}$ hydrocracking are shown in FIG. 6. Negligible conversion of n-$C_{16}$ was observed over SZNi2.0 at 160° C. At 300° C. and above, however, promotion of 0.5 or 2.0 wt % of Ni on SZO results in an appreciable conversion of n-$C_{16}$, although lower than that of SZPt0.5. This is explained by the in situ reduction of nickel oxide present on the fresh catalyst (as confirmed by EXAFS and XANES analyses) to the active metallic state at 300+° C., which is responsible for providing hydrogenation activity and thus avoiding deactivation by coke formation.

The results obtained from the hydrocracking of n-$C_{16}$ over metal-promoted $WO_3$ modified zirconia catalysts (WZOS) for short reaction times are compared with those using metal-promoted SZOs in Table 6. The WZOs show a higher conversion toward hydrocracking of n-$C_{16}$ than do the SZO catalysts. This may be due to inherent activity of the tungstated catalysts or due to the loss of sulfur from the SZO catalysts at the severe reducing conditions [300° C., 500 psig (cold) $H_2$] employed. The product distribution from the tungstated catalysts also shows a high yield of $C_4$–$C_9$ alkanes, indicating a substantial degree of cracking. A Pt/$ZrO_2$/$MoO_3$ catalyst gave only a 5 wt % conversion of n-$C_{16}$ for the same conditions as those in Table 6 perhaps due to the significantly lower acid strength of this catalyst compared to Pt-SZO and Pt-WZO.

TABLE 6

Hydrocracking of n-C16 over Metal-Promoted AZOs

|  | SZPt0.5 | WZPt0.5 | SZNi2.0 | WZNi2.0 |
|---|---|---|---|---|
| conversion | | | | |
| (wt %) | 76.2 | 92.6 | 45.0 | 52.2 |
| product range | yield (wt %) | | | |
| $C_4$–$C_9$ | 61.8 | 72.7 | 39.4 | 38.9 |
| $C_{10}$–$C_{15}$ | 8.2 | 12.9 | 3.2 | 7.0 |
| iso-$C_{16}$ | 6.2 | 7.1 | 2.4 | 6.3 |

[a] Conditions: 300° C., 500 psig (cold) $H_2$, 20 min.

Polyolefins are treated as a separate case as these have long chains of methylene groups and hydrocracking of these to useful products may furnish a way of converting waste polymers to useful transportation fuels. In polyolefin hydrocracking, the viscosity of the polymer melt results in mass transfer limitations and poor $H_2$ diffusion; therefore, experiments had to be conducted at higher temperatures than with n-hexadecane. As with other alkanes, high conversions and high selectivity to gasoline range ($C_5$–$C_{12}$) isoalkanes or to iso-$C_4$ and iso-$C_5$ can be achieved. As indicated earlier, one of the most important parameters in hydrocracking of polyolefins over both $SO_4$—and $WO_3$—modified catalysts is reaction time. Short reaction times (15–25 min) result in a higher yield of $C_5$–$C_{12}$ isoalkanes while longer reaction times (60 min.) produce predominantly $C_1$–$C_5$ light alkanes.

Figure 7:
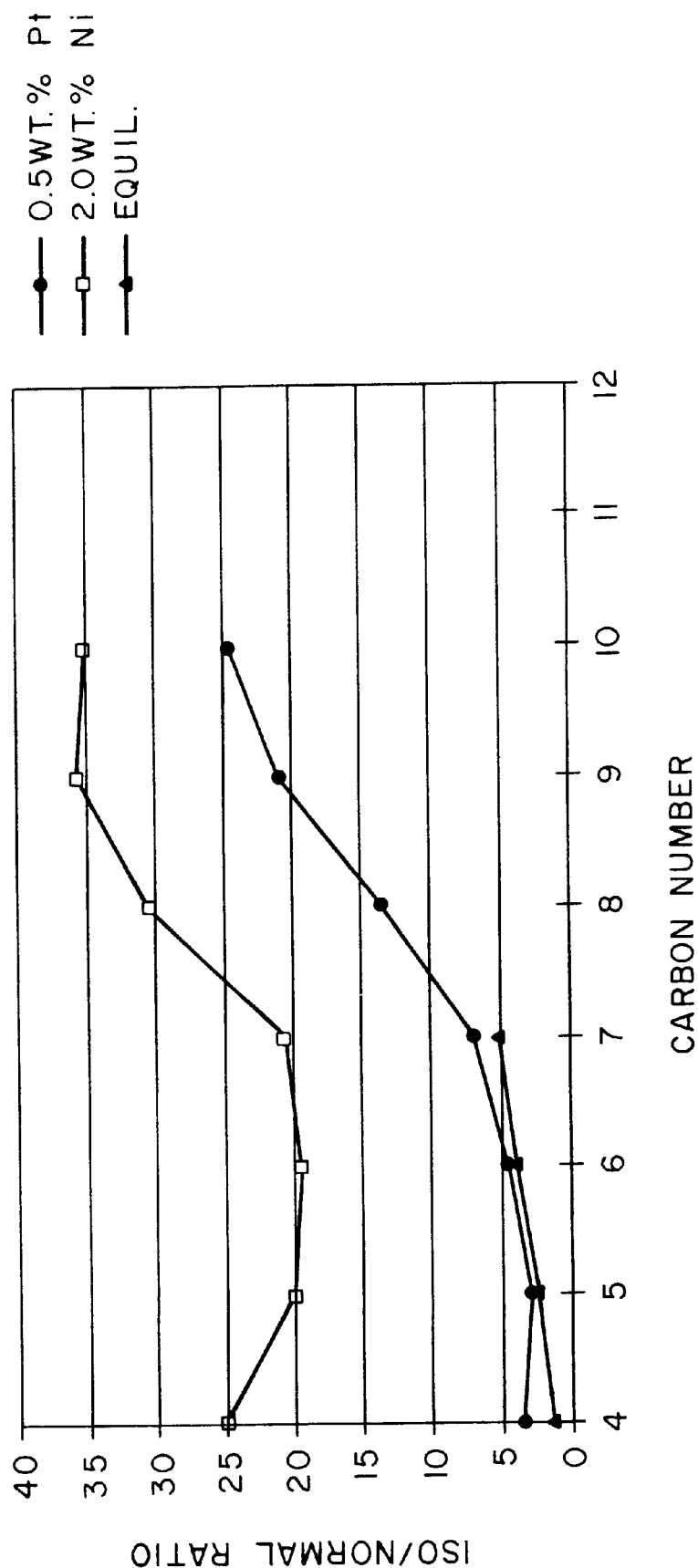
FIG. 7 is a graphical representation of the iso/normal ratios of cracked alkanes obtained from hydrocracking of HDPE over metal-promoted sulfated zirconia (reaction conditions are given in Table 7)

The products obtained from the hydrocracking of HDPE over metal-promoted SZO catalysts are shown in Table 7. More than 98 wt % conversion of the polymer was obtained, giving high yields of gasoline-range products with high ratios of iso/normal alkanes for each carbon number (FIG. 7). Interestingly, promotion with 2 wt% of Ni instead of 0.5 wt % of Pt resulted in products with a higher ratio of iso/normal alkanes at 375° C. As mentioned earlier, the ratio of isomerized to normal alkanes is a function of the balance between the metal promoter and the acid components of AZOs. A postulated role of Pt in the catalysts under hydrogen pressures is to dissociate molecular hydrogen into H atoms which then spillover onto acid sites forming protons and hydride ions. While protons can replenish Bronsted acid sites, the hydride ions can quench carbocation intermediates. The lower hydrogenation activity of nickel compared to platinum (FIG. 6) is responsible for a correspondingly lower concentration of hydride ions on the catalyst surface; the intermediate carbocations could therefore undergo a higher degree of skeletal transformation before desorption from the active sites by hydride transfer.

TABLE 7

Carbon Number Ranges of Products Obtained From HDPE Hydrocracking

|  | yield (wt %) obtained with | |
|---|---|---|
|  | SZPt0.5 | SZNi2.0 |
| conversion (wt %) | 99 | 98 |
| product range | | |
| $C_1$–$C_5$ | 35 | 30 |
| $C_6$–$C_{12}$ range | 63.7 | 65.6 |
| $C_{13}$–$C_{20}$ range | 0.3 | 2.4 |
| $C_{21}$–and above | tr[b] | tr |

[a] conditions were 375° C., 1200 psig (cold) $H_2$, 25 min. [b]Trace

The WZPt0.5 catalyst was also active for the hydrocracking and hydroisomerization of HDPE, resulting in high yields of gasoline-range isoalkanes or high selectivities to iso-$C_4$ and iso-$C_5$ (Table 8). The iso/normal ratios of alkanes are lower with the tungstated catalyst than with the sulfated catalyst. Smaller amounts of $C_1$–$C_5$ alkanes were produced in the WZPt0.5 catalyzed reaction with a correspondingly larger yield of gasoline-range alkanes. This may be due to the lower acid strength of WZPt0.5, reportedly responsible for its lower tendency to cracking compared to SZPt0.5, see E. Iglesia et al. *Abstr. 14th North American Meeting,* The Catalysis Society, Snowbird, Utah, 1995. Using cleavage of diphenylmethane its a measure of Bronsted acid strength, we also found that WZO is weaker than SZO, see K. R. Venkatesh et al., *Energy & Fuels* 1995, 9, 888.

TABLE 8

Iso/n-Alkane Yields of Liquid Products Obtained From HDPE Hydrocracking[a]

| catalyst | SZPt0.5 | WZPt0.5 |
|---|---|---|
| conversion (wt %) | 99 | 98 |
| yield; of $C_1$–$C_5$ gases (wt %) | 41.7 | 32.1 |
| yield of $C_6$–$C_{12}$ alkanes (wt %) | 57.0 | 65.9 |
| alkane | iso/normal ratio | |
| $C_4$ | 3.6 | 2.7 |
| $C_5$ | 2.9 | 1.9 |
| $C_6$[b] | 4.4 | 3.1 |
| $C_7$[b] | 6.7 | 5.5 |
| $C_8$[b] | 6.7 | 7.6 |
| $C_9$ | 20.7 | 11.6 |
| $C_{10}$ | 24 | 12.2 |
| $C_{11}$ | 1.0/tr[c] | 12 |
| $C_{12}$ | tr | 12 |
| $C_{13}$ | tr | 0.2/tr |
| $C_{14}$ and above | | |

[a]Conditions were 375° C., 1200 psig (cold) $H_2$, 25 min. [b]Excluding small amounts of cycloalkanes formed. [c]Trace.

PP could be hydrocracked almost completely at a lower temperature (325° C.) than required for HDPE over the metal-promoted AZO catalysts (Table 9) with high yields of $C_4$–$C_9$ branched alkanes. The ratios of branched to normal alkane products obtained from PP hydrocracking were higher than those obtained from HDPE due to branching of a methyl group at alternate carbon atoms in PP (Table 10).

TABLE 9

PP Hydrocracking over Metal-Promoted SZOs[a]

| | yield (wt %) obtained with | |
|---|---|---|
| | SZPt0.5 | SZNi2.0 |
| product range | | |
| $C_1$–$C_5$ alkanes | 28.1 | 28.5 |
| $C_6$–$C_{12}$ range | 71.7 | 67.0 |
| $C_{13}$–$C_{20}$ range | 5.2 | 4.5 |
| $C_{21}$ and above | tr[b] | tr |

Figure 8:
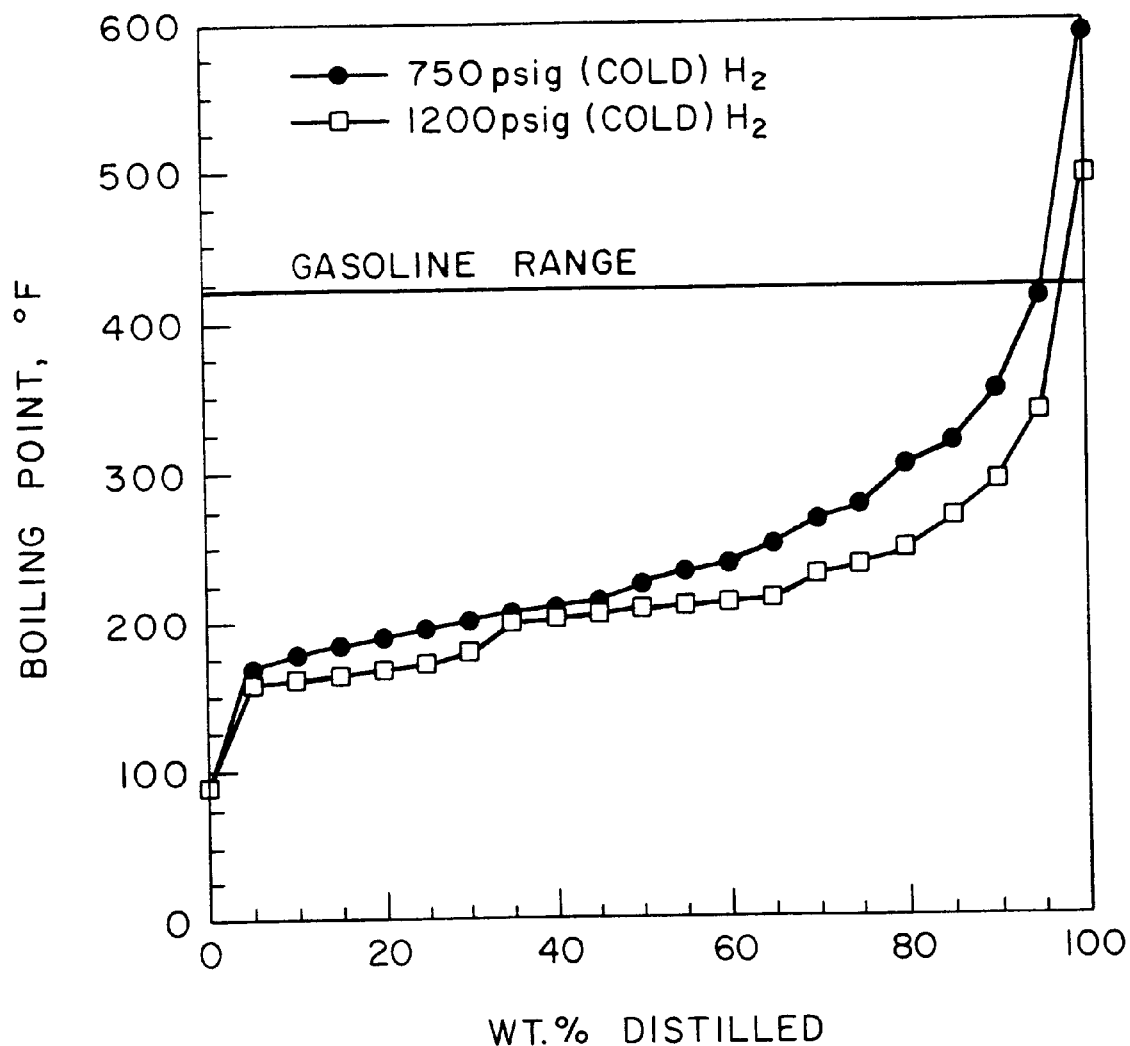
FIG. 8 is a graphical representation of the simulated distillation of liquid products from HDPE hydrocracking over SZPt0.5 (reactions at 375° C. and 25 min. reaction time)
Figure 9:
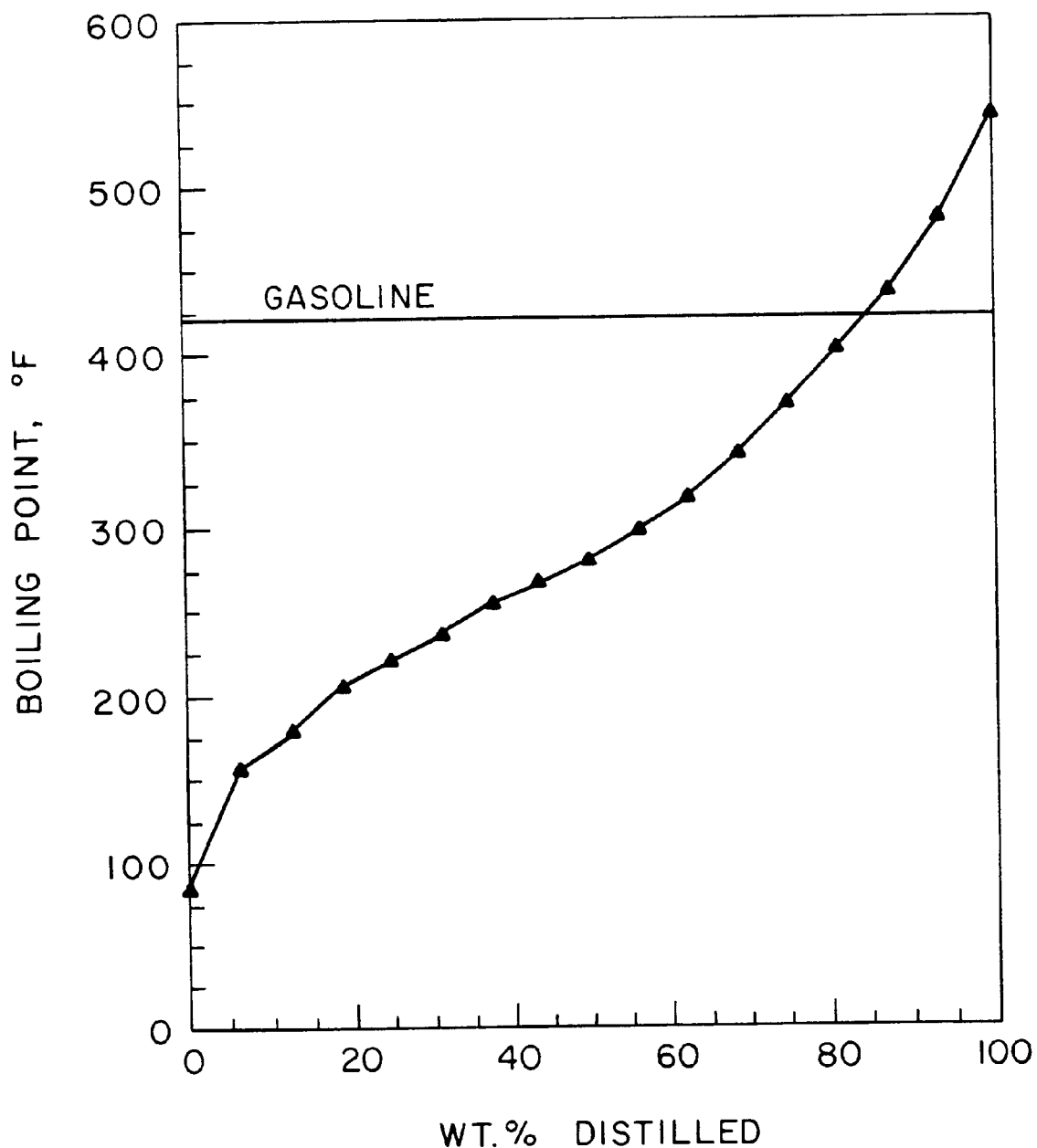
FIG. 9 is a graphical representation of the boiling point distribution of products from polypropylene hydrocracking over SZPt0.5 at 325° C., 750 psig (cold) $H_2$, 20 min.

Conditions were 325° C., 1200 psig (cold) $H_2$, 20 min.; 0.5 wt % of Pt and 2.0 wt % of Ni were impregnated on the catalysts. [b]Trace Simulated distillation of the products obtained from HDPE and PP hydrocracking confirm the results given in Tables 7–9. As shown in FIGS. 8 and 9, more than 85 wt % of the products from HDPE and PP are in the gasoline range (below 421° F. (216° C.)) with the rest in the diesel range (421–650° F. (216–343° C.)). A substantial reduction in initial hydrogen pressure (from 1200 psig to 750 psig) in HDPE hydrocracking resulted in only a small change in the distillable quality of the liquid products obtained (FIG. 8).

TABLE 10

Analysis of Liquid Products from PP Hydrocracking over SZPt0.5[a]

| | selectivity (wt %) | |
|---|---|---|
| alkane | branched isomers | straight chain |
| $C_4$ | 5.3 | 0.3 |
| $C_5$ | 12.2 | 0.4 |
| $C_6$ | 14.7 | 0.4 |
| $C_7$ | 14.6 | 0.3 |
| c-$C_7$[b] | 0.7 | |
| $C_8$ | 14.3 | 0.2 |
| c-$C_8$ | 0.3 | |
| $C_9$ | 11.3 | 0.3 |
| c-$C_9$ | 0.4 | |
| $C_{10}$ | 8.6 | 0.1 |
| $C_{11}$ | 5.7 | tr[c] |
| $C_{12}$ | 5.1 | tr |
| $C_{13}$ | 2.9 | tr |
| $C_{14}$ and above | 1.8 | tr |
| total | 97.9 | 2.0 |

[a]Conditions were 375° C., 750 psig (cold) H2, 20 min. [b]C, cyclic. [c]Trace.

Results from hydrocracking of HDPE over an SZPt0.5 catalyst for two different reaction times are shown in Table 11. The main effect of increased reaction time is the increased yield of light $C_1$–$C_5$ alkanes (from 41.7 to 95.4 wt %), with a corresponding loss in $C_6$+ alkane yields. Although the gas yields differed significantly, the products show a consistently high selectivity toward isobutane and isopentane, indicating that these reactions are kinetically controlled. PP can also be hydrocracked to isobutane and isopentane with high yields over Pt-SZO and Pt-WZO catalysts (Table 12). The selectivities to methane and ethane or lower than PP than with HDPE, possibly due to reaction at lower temperatures. Polystyrene (PS) could be hydrocracked at as low as 300° C. over a SZPt0.5 catalyst resulting in $C_1$–$C_5$ alkylsubstituted aromatics and bicyclic compounds (Table 13).

TABLE 11

HDPE Yields Isobutane and Isopentane With High Selectivity at Different Overall Gas Yields Over a SZPt0.5 Catalyst[a]

| | reaction time | |
|---|---|---|
| | 25 min | 60 min |
| product range | yield (wt %) | |
| $C_6$–$C_{20}$ alkanes | 57.3 | 3.6 |
| $C_1$–$C_5$ alkanes | 41.7 | 95.4 |
| product | selectivity (mol %) | |
| methane + ethane | 3.7 | 6.4 |
| propane | 4.2 | 5.0 |
| isobutane | 37.4 | 44.3 |
| n-butane | 5.6 | 13.0 |
| isopentane | 38.4 | 22.7 |
| n-pentane | 10.7 | 8.6 |

[a]Conditions: 325° C., 1200 psig; (cold) $H_2$, 60 min. feed/cat. 5/1, PP conversion was about ~ 100 wt % in both reactions.

TABLE 12

Hydrocracking of PP to Isobutane and Isopentane over Sulfated and Tungstated AZOs.[a]

| | yield (wt %) obtained with | |
|---|---|---|
| | SZPt0.5 | WZPt0.5 |
| product range | | |
| $C_6$–$C_{20}$ alkanes | 8.7 | 49.7 |
| $C_1$–$C_5$ alkanes | 91.3 | 50.3 |
| product | selectivity (mol %) | |
| methane + ethane | 0.8 | 0.5 |
| propane | 1.0 | 0.8 |
| isobutane | 29.9 | 24.5 |
| n-butane | 14.3 | 13.5 |
| isopentane | 45.2 | 48.6 |
| n-pentane | 8.8 | 12.1 |

[a]Conditions: 325° C., 1200 psig; (cold) $H_2$, 60 min. feed/cat. 5/1 PP conversion was ~ 100 wt % in both reactions.

TABLE 13

Hydrocracking of PS over a SZPt0.5 Catalyst[a]

| Product | yield (wt %) | product | yield (wt %) |
|---|---|---|---|
| benzene | 15.50 | C5-substituted benzenes | 2.12 |
| toluene | 1.59 | C2-substituted indanes | 6.20 |
| C2-substituted benzenes | 11.98 | tetralin | 2.09 |
| C3-substituted benzenes | 12.89 | methyltetralins | 1.72 |
| indane | 8.42 | C2-substituted tetralins | 1.66 |
| C1-substituted indanes | 15.27 | diphenylmethane | 0.87 |
| C4-substituted benzenes | 3.77 | unidentified | 15.92 |

[a]Reaction conditions: 300° C., 1200 psig (cold) $H_2$, 60 min. conversion was ~ 100 wt %.

Figure 10:
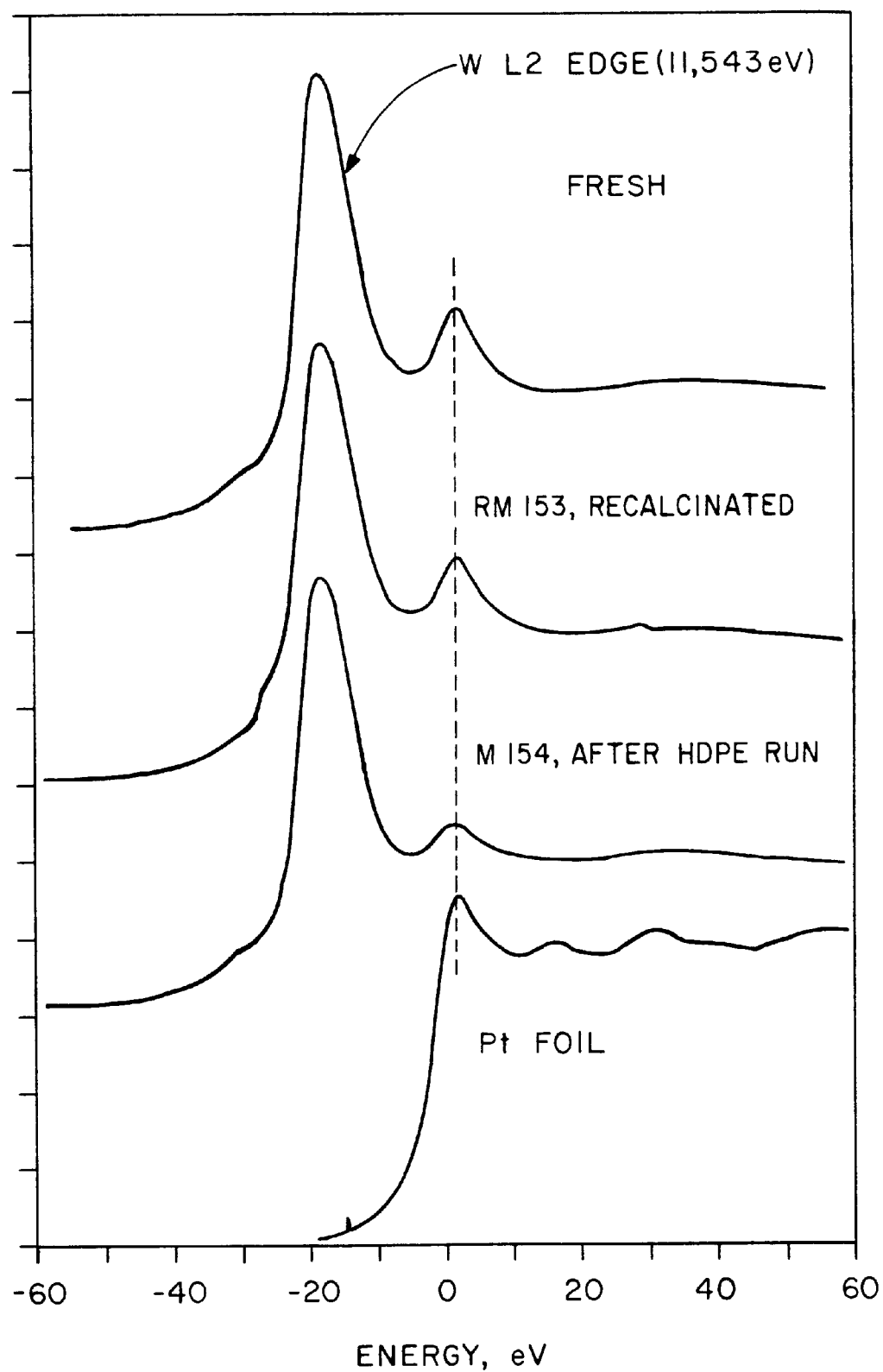
FIG. 10 is a graphical representation of the Pt $L_3$ edge (11,564 eV) XANES spectra of fresh, recovered and recalcined WZPt0.5 catalysts.

The catalysts recovered from some of the hydrocracking reactions at the severe reducing conditions [325–375° C., 750–1200 psig (cold) $H_2$] were analyzed to determine the fate of the anionic groups (Table 14.) The SZPt0.5 catalysts lost a substantial portion of the starting sulfur content, indicating that reduction of the surface sulfate groups to $SO_x$ and even to $H_2S$ (odor-apparent) had occurred during reaction. Sulfur loss from sulfated zirconia catalysts in n-butane isomerization at 250° C. as well as in n-octane hydrocracking reactions at 250° C. and above under $H_2$ pressure has recently been reported, see F. T. T. Ng et al., *Appl. Catal.* A 1995, 123, L197 and R. Mao Le Van et al., *Catal. Lett.* 1995, 35, 107. Sulfur loss is higher in hydrocracking reactions at higher temperatures and is not as severely affected by $H_2$ pressures, indicating that it is more dependent on reaction temperature than on $H_2$ pressure. However, the tungsten content of the $WO_3$-modified catalyst was not appreciably affected by reaction at 375° C. under 1200 psig (cold) $H_2$. The loss indicated in Table 14 in tungsten content is largely due to the observed organic content on the recovered catalyst (4.51 wt %) found by recalcining WZPt0.5 at 500° C. in air. After the organic content was accounted for, the tungsten loss on the recovered WZPt0.5 was calculated to be 0.05 wt % which is within experimental error. Comparison of XRD average particle sizes of the fresh and recovered SZPt0.5 and WZPt0.5 catalysts indicated that, within a ±5 Å error in particle size, there was no agglomeration or sintering of the metal-promoted AZOs during reaction (Table 14). The WZPt0.5 catalyst recovered from HDPE hydrocracking was recalcined at 500° C. in air for 60 min. XANES spectra were obtained for three catalyst samples: fresh, one recovered after HDPE hydrocracking, and that recalcined after recovery from HDPE reaction. The Pt $L_3$ edge (11,564 eV) XANES results indicate that Pt is present in the metallic ($Pt^0$) state on these catalysts, consistent with the peak position of standard Pt foil (FIG. 10). The same conclusion was reached earlier by others about the state of Pt on Pt promoted SAO, see A. Sayari et al. *J. Catal.* 1994, 145, 561k. The zerovalent state of Pt is maintained, even on fresh (calcined at 700° C. in air) as well as with recalcined Pt-WZO catalysts. The peak at –18 eV in FIG. 10 corresponds to the W $L_2$ edge at 11 5432 eV.

TABLE 14

Stability and Particle Size of Fresh and Recovered Catalyst

| | | S or W content (wt %) | | av particle size (Å) | |
|---|---|---|---|---|---|
| catalyst | reaction details | before | after | before | after |
| SZPt0.5 | HDPE, 375° C., 1200 psig (cold) $H_2$, 25 min | 1.63 | 1.07 | 90 ± 5 | 90 ± 5 |
| | HDPE, 375° C., 750 psig (cold) $H_2$, 25 min | 1.63 | 1.08 | | |
| | PP, 325° C., 1200 psig (cold) $H_2$, 20 min | 1.63 | 1.32 | | |
| WZPt0.5 | HDPE, 375° C., 1200 psig (cold) $H_2$, 25 min | 7.07 | 6.70 | 92 ± 5 | 85 ± 5 |

Figure 11:
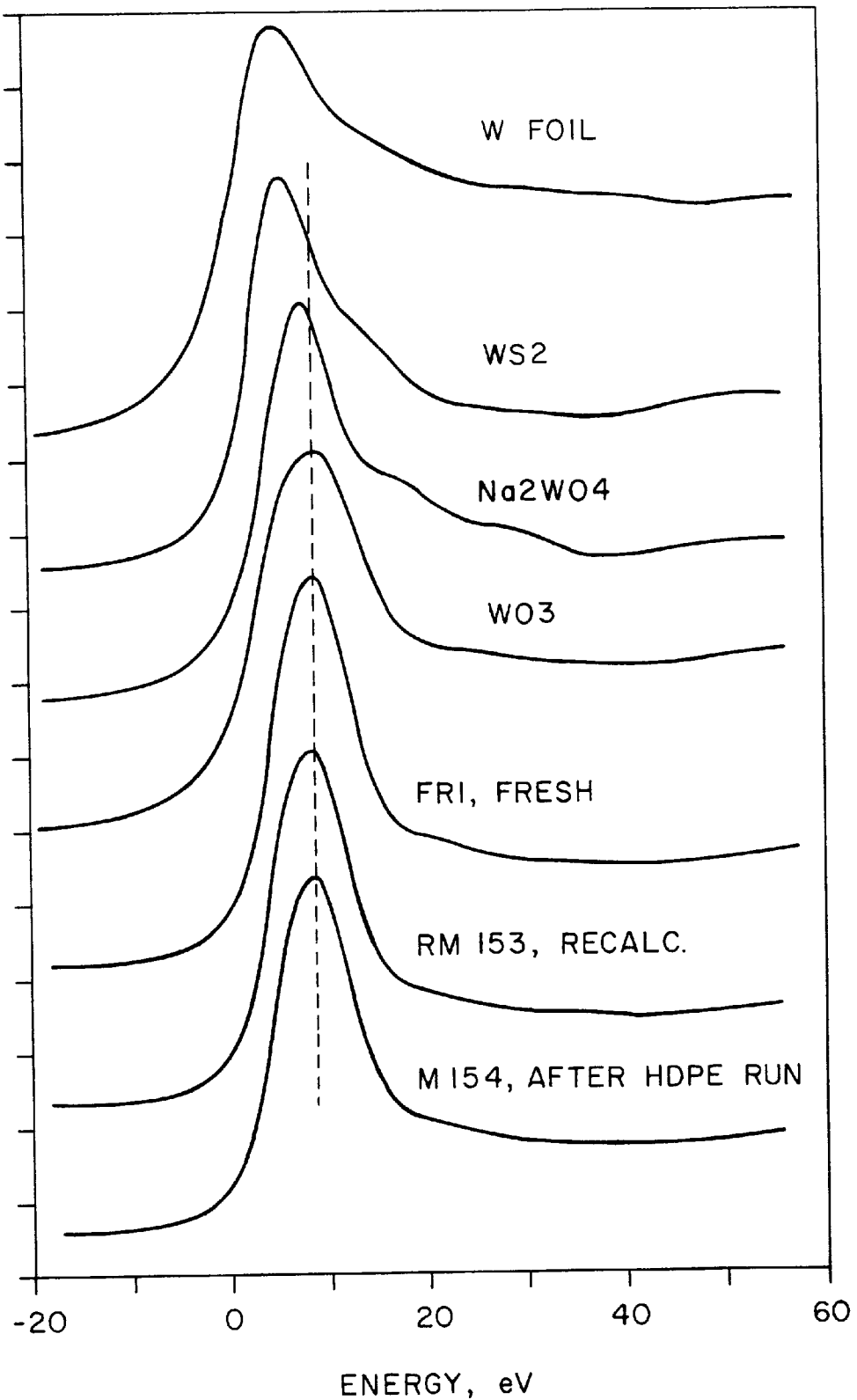
FIG. 11 is a graphical representation of the W $L_3$ edge (10,207 eV) XANES spectra of the WZPt0.5 catalysts and various tungsten standards.

Analysis of the $WL_3$ edge (10,207n eV) XANES spectra (FIG. 11) indicates that W is present only in its hexavalent ($W^{6+}$) state on the catalyst surface, as seen by the fact that it occupies the same position on the catalyst as on the $WO_3$ standard. The XANES results, along with XRD profiles of recovered Pt-WZO, indicate that, unlike $SO_4$, $WO_3$ is not reduced to an appreciable extent on the catalyst surface even after reactions at severe reducing conditions.

Summarizing, metal-impregnated AZOs are environmentally benign, effective catalysts for the hydrocracking and hydroisomerization of a variety of long-chain alkanes to valuable fuels or fuel components in high yields. Alkanes from n-$C_{20}$ to high molecular weight polyolefins (HDPE, PP, or PS) can be used as feedstocks for these reactions. These reactions may provide a way for the useful conversion of waste polyolefins to transportation fuels. The product distribution from higher alkane hydrocracking can be controlled to obtain either high yields of gasoline-range isoalkanes or high selectivity to isobutane and isopentane. Depending on reaction conditions, Pt-WZO is a catalyst with an activity range comparable to Pt-SZO catalyst for alkane hydrocracking.

The SZO catalysts have questionable long-term stability during severe hydrocracking reactions (at 300+° C.) due to loss of sulfur. On the other hand, the WZO catalysts appear to be stable in reactions at these conditions.

The invention as herein described is particularly adapted to cracking feedstocks of polymers of at least 20 carbon atoms. More particularly, the invention relates to the cracking of polyethylene, both high and low densities, polypropylene, polystyrene, polyolefins, oxygenated polymers, waxes and mixtures thereof. More specifically, the invention applies to polyethylene terephalate, polymethyl methacrylate, polyvinyl acetate and waxes, including Fischer Tropsch waxes.

The metal promoted anion modified metal oxide catalyst may have oxides selected from $ZrO_2$, $HfO_2$, $TiO_2$ and $SnO_2$. $ZrO_2$ and $HfO_2$ are preferred with $ZrO_2$ being most preferred. The catalyst may be promoted by use of any one of a variety of metals well known as promoters in the art. More specifically, applicable metals are Pt, Ni, Pd, Rh, Ir, Ru, (Mn and Fe) or mixtures thereof, preferably present in the range of from about 0.2% to about 15% by weight of the catalyst. Of the above named promoters, Ni and Pt are most preferred with Ni being a promoter of choice due to cost. When Ni is used it is preferably present in the range of from about 2% to about 5% by weight of the catalyst.

The acid catalyst disclosed herein may be modified by anions such as $SO_4$ and $WO_3$, it being understood that $WO_3$ is not anion in the true sense of the word but it is added as an anion to the base metal dioxide catalyst. Where $SO_4$ or $WO_3$ are used they are preferably present in the range of from 0.5% to about 20% by weight of the catalyst. If sulfate is used, it is preferably present in the range of from about 1% to about 10% by weight of the catalyst and if the tungstate is used it is preferably present in the range of from about 3% to about 20% by weight of the catalyst and more preferably in the range of from about 5% to about 15% by weight of the catalyst. The pressure at which the reaction takes place is generally initially in the range of from 200 psig (cold) to about 2000 psig (cold). Most preferably, the initial hydrogen pressure is in the range of from about 300 psig (cold) to about 1200 psig (cold). Preferably the temperature at which the reaction takes place is in the range of from about 100 to about 600° C. and most preferably the temperature is in the range of from about 130° C. to about 400° C.

In its more preferred embodiment, the weight ratio of feedstock to catalyst is in the range of from about 12 parts of feedstock to about 1 part of catalyst. The specific weight ratio of feedstock to catalyst is in the range of from about 1 part to about 6 parts of feedstock to one part of catalyst. The time during which the feedstock is in contact with the catalyst at the appropriate temperature and pressure is important. Preferably, the feedstock is in contact with the catalyst for a time in the range of from about ten minutes to about 2 hours. Obviously, the shorter the amount of time that the feedstock is in contact with the catalyst the more economic the process.

The preferred time range is in the range of about 20 minutes to one hour.

While there has been disclosed what is considered to be the preferred embodiment of the present invention, it is understood that various changes in the details may be made without departing from the spirit, or sacrificing any of the advantages of the present invention.

The embodiments of the invention in which an exclusive property or privilege is claimed are defined as follows:

1. A method of cracking and isomerizing a hydrocarbon feedstock comprising contacting the feedstock with a metal-promoted anion-modified metal oxide catalyst in the presence of hydrogen gas at a sufficient pressure and at a temperature from greater than about 300° C. to about 600° C. and for a time sufficient to crack and isomerize the feedstock, wherein the metal oxide of the catalyst is one or more of $ZrO_2$, $HfO_2$, $TiO_2$ and $SnO_2$, and wherein the anion is $WO_3$ and the feedstock is principally hydrocarbon chains of at least 32 carbon atoms.

2. The method of claim 1, wherein the metal-promoted anion-modified metal oxide catalyst contains one or more of Pt, Ni, Pd, Rh, Ir, Ru, Mn and Fe in combination or mixtures thereof present in the range of from about 0.2% to about 15% by weight of the catalyst.

3. The method of claim 1, wherein the metal-promoted anion-modified metal oxide catalyst contains Ni present in the range of from about 2% to about 5% by weight of the catalyst.

4. The method of claim 1, wherein the metal-promoted anion-modified metal oxide catalyst contains $WO_3$ present in the range of from about 3% to about 20% by weight of the catalyst.

5. The method of claim 1, wherein the metal-promoted anion-modified metal oxide catalyst contains $WO_3$ present in the range of from about 5% to about 15% by weight of the catalyst.

6. The method of claim 5, wherein the hydrogen pressure is in the range of from about 300 psig (cold) to about 1200 psig (cold).

7. The method of claim 6, wherein the contact between the feedstock and the catalyst takes place at a temperature in the range of from about greater than about 300° C. to about 400° C.

8. The method of claim 7, wherein the weight ratio of feedstock to catalyst is from about 2 to about 6:1.

9. The method of claim 8, wherein the feedstock is maintained in contact with the catalyst for a time in the range of from about 20 minutes to one hour.

10. The method of claim 9, wherein the feedstock principally contains one or more of polypropylene, polystyrene, polyethylene, polyethylene terephathalate, polymethyl methacrylate, and polyvinyl acetate.

11. The method of claim 8, wherein the feedstock principally contains one or more of high density polyethylene, low density polyethylene, polypropylene and polystyrene.

12. The method of claim 6, wherein the weight ratio of feedstock to catalyst is up to about 12:1.

13. The method of claim 5, wherein the feedstock is maintained in contact with the catalyst for a time in the range of from about 10 minutes to about 2 hours.

14. The method of claim 1, wherein the contact between the feedstock and the catalyst takes place at a hydrogen pressure in the range of from about 200 psig (cold) to about 2500 psig (cold).

15. The method of claim 1, wherein the metal-promoted anion-modified metal oxide catalyst contains $WO_3$ in the range of from about 0.5% to about 20% by weight of the catalyst.

16. A method of cracking and isomerizing a hydrocarbon feedstock selected from hycarbon chains of $C_{32}$ or higher and molecular weights greater than about 500 comprising contacting the feedstock with an anion-modified metal oxide catalyst wherein the metal oxide is selected from the group consisting of $ZrO_2$, $HfO_2$, $TiO_2$ and mixtures thereof in the presence of hydrogen gas at a pressure of not less than about 100 psig (cold) at a temperature from greater than about 300° C. to about 600° C. and for a time sufficient to crack and isomerize the feedstock, wherein the anion is $WO_3$ and the anion-modified metal oxide catalyst is promoted with Pt, Ni, Pd, Rh, Fr, Ru, and Mn and Fe in combination or mixtures thereof.

17. The method of claim 16, wherein the catalyst is promoted with Pt or Ni.

18. The method of claim 17, wherein the weight ratio of feedstock to catalyst is in the range of about 1 to about 6 parts feedstock to about one part catalyst.

19. The method of claim 18, wherein the metal oxide catalyst contains $ZrO_2$ promoted with Ni and modified with $WO_3$.

20. The method of claim 19, wherein the feedstock is principally selected from long-chain alkanes, polyolefins, oxygenated polymers, waxes and mixtures thereof.

21. A method of cracking and isomerizing a hydrocarbon feedstock containing hydrocarbon chains of $C_{32}$ or higher and selected from polyethylene, polypropylene, polystyrene, polyolefins, oxygenated polymers, waxes and mixtures thereof comprising contacting the feedstock with an anion-modified metal oxide catalyst promoted with Pt, Ni or mixtures thereof in the presence of hydrogen gas at an initial pressure of not less than about 100 psig at a temperature from greater than about 300° C. to less than about 600° C. and for a time sufficient to crack and isomerize the feedstock, wherein the metal oxide is one or more of $ZrO_2$ and $HfO_2$, and the metal oxide catalyst is modified with $WO_3$.

22. The method of claim 21, wherein the feedstock principally contains one or more of polypropylene, polystyrene, polyethylene, polyethylene terephalate, polymethyl methacrylate, polyvinyl acetate and waxes.

23. The method of claim 22, wherein the feedstock contains principally Fishcher-Tropsch waxes.

24. The method of claim 21, wherein the feedstock is in contact with the catalyst for a time in the range of from about 10 minutes to about 2 hours.

25. The method of claim 24, wherein the hydrogen pressure is in the range of from about 300 psig (cold) to about 1200 psig (cold), the temperature is in the range of from about greater than about 300° C. to about 400° C., and the time is in the range of from about 20 minutes to about 1 hour.

26. The method of claim 25, wherein the catalyst is $ZrO_2$ modified with $WO_3$ present of from about 5% to about 15% of the catalyst and promoted with Ni present in the range of from about 2% to about 5% by weight of the catalyst.

27. A method of cracking and isomerizing a hydrocarbon feedstock which comprises contacting the feedstock with a catalyst in the presence of hydrogen gas at a sufficient pressure and at a temperature from greater than about 300° C. to about 600° C. and for a time sufficient to crack and isomerize the feedstock; wherein the catalyst consists essentially of a metal-promoted anion-modified metal oxide catalyst, the metal oxide of the catalyst is one or more of $ZrO_2$, $HfO_2$, $TiO_2$ and $SnO_2$, the anion is $WO_3$, and the metal promoter is Pt, Ni, Pd, Rh, Ir, Ru and Mn and Fe in combination or mixtures thereof; and the feedstock is principally hydrocarbon chains of at least 32 carbon atoms.

* * * * *